United States Patent
Shou et al.

(10) Patent No.: US 8,551,147 B2
(45) Date of Patent: Oct. 8, 2013

(54) HYPERTENSION THERAPY INSTRUMENT AND METHOD FOR TREATING HYPERTENSION

(75) Inventors: Zhanggen Shou, Hangzhou (CN); Renzhao Wu, Hangzhou (CN)

(73) Assignee: Hangzhou Dalishen Medical Device Ltd., Hangzhou, Zhejiang Provine (CN)

( * ) Notice: Subject to any disclaimer, the term of this patent is extended or adjusted under 35 U.S.C. 154(b) by 1164 days.

(21) Appl. No.: 12/475,603

(22) Filed: Jun. 1, 2009

(65) Prior Publication Data

US 2010/0305667 A1   Dec. 2, 2010

(51) Int. Cl.
*A61N 1/39* (2006.01)
*A61N 5/06* (2006.01)

(52) U.S. Cl.
USPC .............................................. 607/88; 607/1

(58) Field of Classification Search
USPC ........ 607/88–94, 100, 1; 606/9; 600/481, 483
See application file for complete search history.

(56) References Cited

U.S. PATENT DOCUMENTS

| | | | | |
|---|---|---|---|---|
| 4,777,961 A * | 10/1988 | Saltzman | ...................... | 600/528 |
| 4,800,495 A * | 1/1989 | Smith | ........................... | 600/322 |
| 6,840,955 B2 * | 1/2005 | Ein | ............................... | 607/108 |
| 7,033,382 B2 * | 4/2006 | Lach | .............................. | 607/89 |
| 7,052,167 B2 * | 5/2006 | Vanderschuit | ................ | 362/572 |
| 7,674,231 B2 * | 3/2010 | McCombie et al. | .......... | 600/485 |
| 7,785,358 B2 * | 8/2010 | Lach | .............................. | 607/89 |
| 2002/0010500 A1 * | 1/2002 | Chen | .............................. | 607/89 |
| 2002/0026226 A1 * | 2/2002 | Ein | ............................... | 607/108 |
| 2006/0287603 A1 * | 12/2006 | Bartnik et al. | ................ | 600/504 |

* cited by examiner

*Primary Examiner* — Yogesh Patel

(57) ABSTRACT

A hypertension therapy instrument comprises an infrared ray generator that can radiate infrared ray onto a human body; a heart rhythm signal generator sensing heart rhythm of the human body and outputs a heart rhythm signal containing heart rhythm information; a controlling device receiving the signal outputted by the heart rhythm signal generator and controlling a radiation intensity of the infrared ray generator based on the heart rhythm of the human body, so that the radiation intensity of the infrared ray generator changes with the heart rhythm of the human body, so as to treat hypertension; and a power supply supplying power to the infrared ray generator, the heart rhythm generator, and the controlling device.

16 Claims, 2 Drawing Sheets

HYPERTENSION THERAPY INSTRUMENT AND METHOD FOR TREATING HYPERTENSION

BACKGROUND OF THE PRESENT INVENTION

1. Field of Invention

The present invention relates to a therapy instrument, and more particularly to a hypertension therapy instrument comprising an infrared ray generator whose radiation intensity is adjusted in real time based on the heart rhythm of a human body.

2. Description of Related Arts

Hypertension, or high blood pressure, is a 'risk factor' for developing a cardiovascular disease (such as a heart attack or stroke), and kidney damage, sometime in the future. If you have high blood pressure, over the years it may do some damage to your arteries and put a strain on your heart. In general, the higher your blood pressure is, the greater the health risks.

Treatment includes a change in lifestyle risk factors where these can be improved—losing weight if you are overweight, regular physical activity, a healthy diet, cutting back if you drink a lot of alcohol, stopping smoking, and a low salt and caffeine intake. If needed, medication can lower blood pressure.

Many kinds of drugs can lower high blood pressure, such as western medicine and Chinese traditional medicine and so on. However, taking medicine for long time shall bring huge side effects and drug resistance, and the effect is not always ideal and cannot be consolidated. Some medicines are only suitable for a specific a group of people. Therefore, some kinds of hypertension therapy instruments have been developed to lower high blood pressure. This therapy instrument surpasses medicine, since the latter one is a stress therapy that cannot cure the pathogeny of the disease.

It is a thousands years of history to treat the hypertension on the therapy point in the ear in China. Ear is a miniature of a whole human body, each organ of the human body has a relative point on the ear, Chinese medicine call it as 'point', Treating on the relative points, the disease can be treated. Hypertension is caused by many kinds of reasons. The sympathetic nerve is excited and adrenaline Epinephrine raise is the important reason. Treating on the relative points of the ear, it can adjust the disorder of the excited sympathetic nerve and low the adrenaline Epinephrine raise. Find the therapy points on the ear then put the therapy machine on the points. This machine is easy for using and safe.

The mechanism of reducing blood pressure by laser irradiation is: change the aggregation of red blood cell and red platelet and promote dissolution of fibrinogen in plasma through laser irradiation, in order to reduce blood viscosity and peripheral resistance. In addition, laser irradiation can reduce lipid content in blood, and improve vessel elasticity and blood viscosity. From this we can see that irradiating blood by laser is an effective way to cure hypertension radically.

SUMMARY OF THE PRESENT INVENTION

An object of the present invention is to provide hypertension therapy instrument comprising an infrared ray generator whose radiation intensity is adjusted in real time based on the heart rhythm of a human body so as to treat hypertension of a human body.

Another object of the present invention is to provide a method for treating hypertension. This method can not only lower high blood pressure, but also can improve the function of the organs of the human body.

Accordingly, in order to accomplish the above object, the present invention provides a hypertension therapy instrument comprising:

an infrared ray generator that can radiate infrared ray onto a human body;

a heart rhythm signal generator sensing heart rhythm of the human body and outputs a heart rhythm signal containing heart rhythm information;

a controlling device receiving the signal outputted by the heart rhythm signal generator and controlling a radiation intensity of the infrared ray generator based on the heart rhythm of the human body, so that the radiation intensity of the infrared ray generator changes with the heart rhythm of the human body, so as to treat hypertension; and a power supply supplying power to the infrared ray generator, the heart rhythm generator, and the controlling circuit.

These and other objectives, features, and advantages of the present invention will become apparent from the following detailed description, the accompanying drawings, and the appended claims.

DETAILED DESCRIPTION OF THE PREFERRED EMBODIMENT

Figure 1:
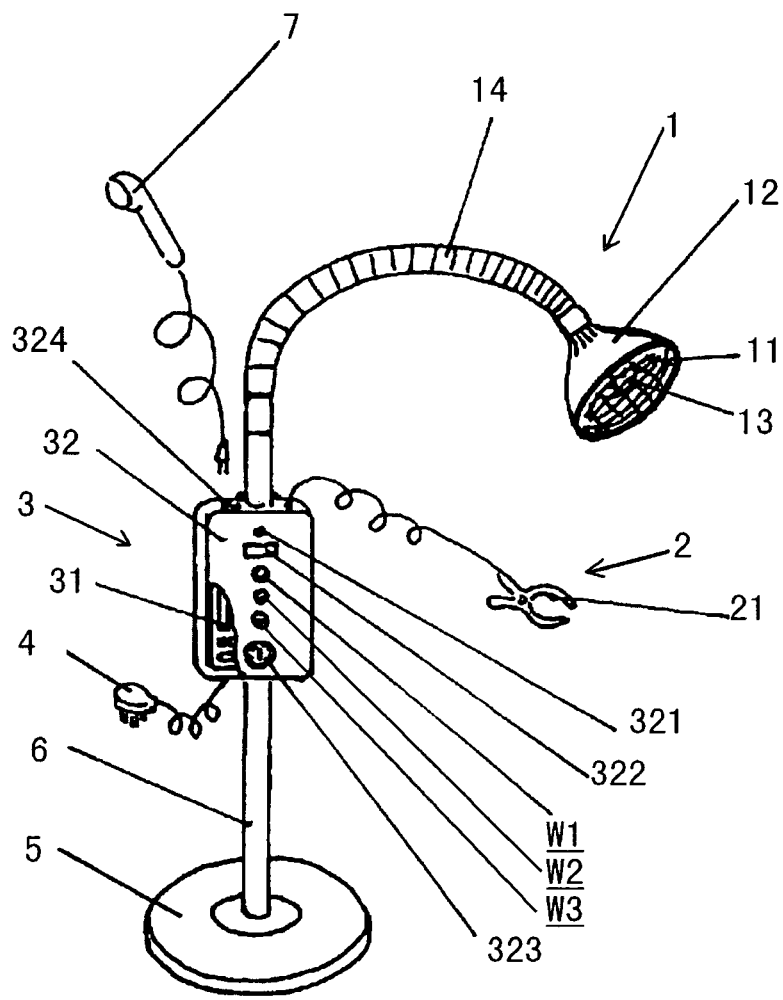
FIG. 1 is a perspective view of hypertension therapy instrument according to a preferred embodiment of the present invention.

Referring to FIG. 1 of the drawings, a hypertension therapy instrument according to a preferred embodiment of the present invention is illustrated, in which the hypertension therapy instrument comprises an infrared ray generator 1, a heart rhythm generator 2, a controlling device 3 and a power supply 4.

The infrared ray generator 1 is embodied as an infrared ray lamp in this preferred embodiment, which can radiate infrared ray onto a human body. The infrared ray lamp may adopt tungsten or other infrared ray radiator for radiating infrared ray. The infrared ray lamp comprises a lamp bulb 11, a lamp shade 12 surrounding the lamp bulb 11, a mesh cover 13 mounted in front of the lamp shade 12 to cover a front side of the lamp bulb 11, and an extending neck 14 having one end extending from the back of the lamp shade and having the other end connecting with the controlling device.

The heart rhythm signal generator 2 senses heart rhythm of the human body and outputs a heart rhythm signal containing heart rhythm information. In one embodiment, the heart rhythm signal generator comprises an electret condenser microphone 21 to sense the heart rhythm of the human body via radial pulse or finger pulse. In another embodiment, the heart rhythm signal generator comprises a luminotron and a photosensitive tube, which can be put on a finger of a human body to sense pulse on the finger and output a heart rhythm signal containing heart rhythm information.

The controlling device 3 comprises a controlling circuit receiving the signal outputted by the heart rhythm signal generator 2 and controlling a radiation intensity of the infrared ray generator 1 based on the heart rhythm of the human body, so that the radiation intensity of the infrared ray generator 1 changes with the heart rhythm of the human body, so as to treat hypertension.

The power supply 4 supplies power to the infrared ray generator 1, the heart rhythm generator 2, and the controlling device 3.

The hypertension therapy instrument further comprises a base 5 and a supporting frame 6 mounted on the base 5 to supporting the controlling device 3 and the infrared ray generator 1. The controlling device further comprises a control panel 32 mounted outside the controlling circuit. The control panel comprises a working indicator 3121 to indicate the operating status of the hypertension therapy instrument, a switch 322 to turn on or off the power supply, and three knobs $W_1$, $W_2$ and $W_3$ for adjusting the radiation intensity, sensitivity and couple level between the heart rhythm signal generator and infrared ray generator respectively. The control panel further comprises a timer 323 to regulate the operation time of the hypertension therapy instrument.

The hypertension therapy instrument further comprises a massager 7 connected with the control panel via a socket 324 provided on the control panel. The socket is connected with the infrared ray lamp in parallel, so that the strength of the massager can also change with the heart rhythm of a human body.

Figure 2:
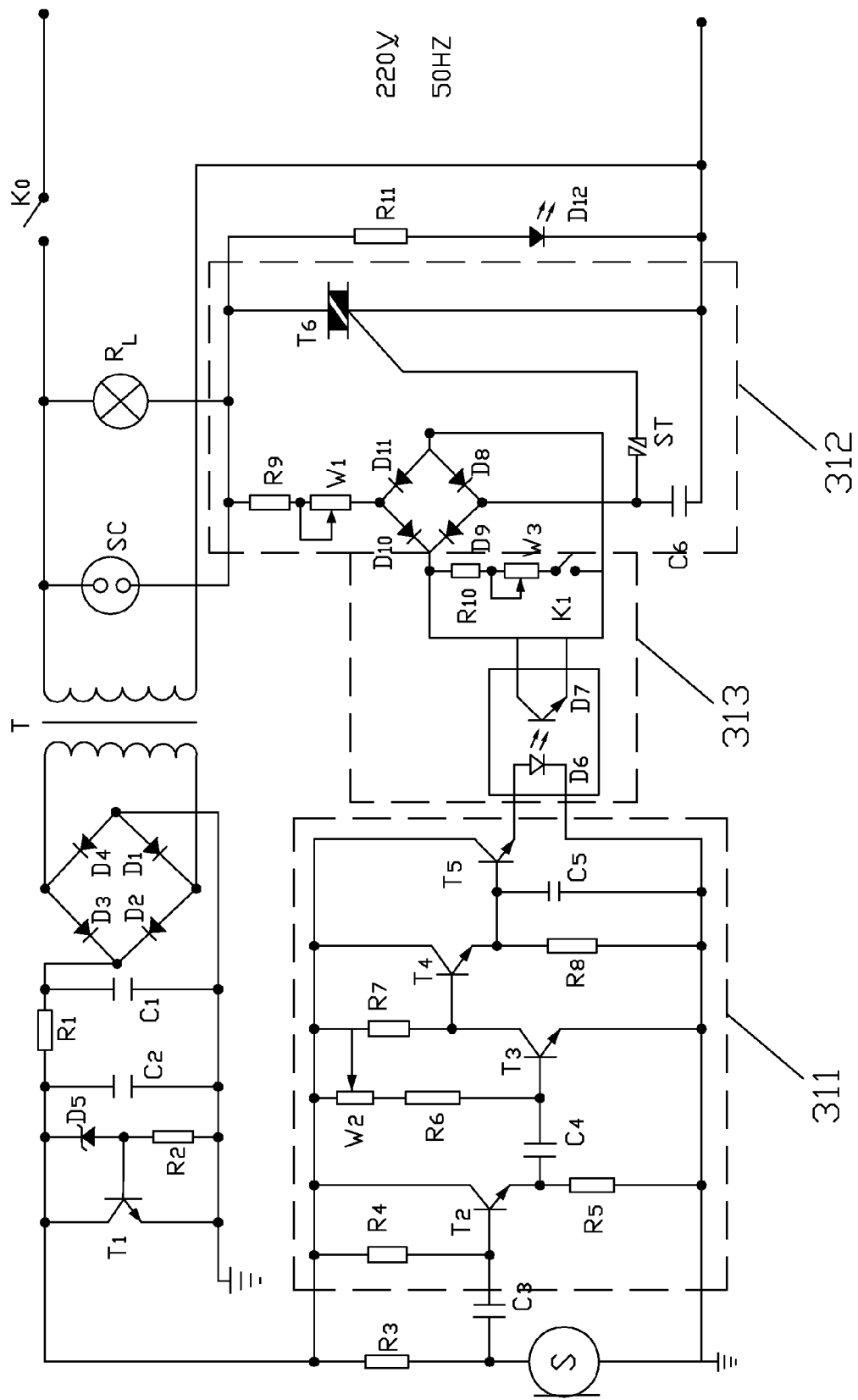
FIG. 2 is a circuit diagram of hypertension therapy instrument according to the above preferred embodiment of the present invention.

Referring to FIG. 2 of the drawings, the power supply is embodied a transformer T and a rectifier circuit so as to provide low voltage DC current to the controlling circuit. The heart rhythm signal generator is embodied as an electret condenser microphone S, the infrared ray generator is embodied as $R_L$, SC connected in parallel with $R_L$ is the socket provided on the control panel, and $K_0$ is the switch as shown in FIG. 2. Furthermore, R11 and D12 is the indicator on the control panel showing the operating status of the hypertension therapy instrument.

Referring to FIG. 2 of the drawings, the controlling circuit 31 comprises an amplifying and filtering circuit 311, an adjusting circuit 312 to adjusting the radiation intensity of the infrared ray generator 1, and an isolation circuit 313 connected between the amplifying and filtering circuit 311 and the adjusting circuit 313.

The amplifying and filtering circuit 311 is to amplify the heart rhythm signal. As shown in FIG. 2, $T_2$ through $T_5$ are transistors to amplify the heart rhythm signal, and $W_2$ is potentiometers to adjust the output level of the amplifying and filtering circuit so as to adjust the sensitivity of hypertension therapy instrument. The amplifying and filtering circuit may also be embodied as an operational amplifier.

The isolation circuit 313 comprises a LED $D_6$ and a photosensitive tube $D_7$ coupled with each other and connected with the amplifying and filtering circuit 311 and the adjusting circuit 312 respectively for outputting the heart rhythm signal and isolating the high voltage and low, voltage for safely purpose. The current on the photosensitive tube $D_7$ is controlled by the LED $D_6$. A resistor $R_{10}$, a potentiometer $W_3$ and a switch $K_1$ connected in series are connected with the photosensitive tube $D_7$ in parallel for controlling the couple level between the LED $D_6$ and the photosensitive tube $D_7$. With the increasing resistance of the potentiometer $W_3$, the potential level increases too.

The adjusting circuit 312 comprises a two-way silicon controlled rectifier (SCR) connecting to the load $R_L$ and then to the AC power supply, a resistor-capacitor phase shifting circuit to control the conduction angle of the SCR so as to adjust the operating voltage of the load $R_L$, and a bridge consisting of $D_8$ through $D_{10}$. The resistor-capacitor phase shifting circuit comprises a resistor $R_9$, a potentiometer $W_1$ and a capacitor $C_6$. The photosensitive tube $D_7$ is connected with the bridge. The output end of the bridge is connected with the resistor-capacitor phase shifting circuit in parallel and the input end of the bridge is connected between the potentiometer $W_1$ and the capacitor $C_6$ in series. The potentiometer $W_1$ can directly control the conduction angle of the two-way silicon controlled rectifier so as to directly control the output power of the infrared ray lamp. ST is a bidirectional switch diode trigger connected with the SCR.

The using method of the hypertension therapy instrument of the present invention is illustrated as follows. Connect the hypertension therapy instrument to power, switch on the switch $K_0$, and the indicator $D_{12}$ is turned on. Put heart rhythm signal generator on the wrist or the finger to sense the heart rhythm of the human body, and put the infrared ray lamp close to the human body, so that the radiation intensity of the infrared ray lamp change with the heart rhythm of the human body so as to treat hypertension of the human.

A method for treating hypertension comprises steps of (a) sensing heart rhythm from a human body; (b) outputting a heart rhythm signal; (c) radiating infrared ray onto a human body; wherein radiation intensity of the infrared ray changes with the heart rhythm of the human body.

A comparative experiment adopts Spontaneously Hypertensive Stroke-Prone Rats (SHR-SP). Divide the Rats into four groups: Group I, Group II, Group III, and Group IV, wherein the blood pressure of Group IV is normal. Treating Group I with the hypertension therapy instrument of the present invention once a day for 12 weeks and then observe the Group I for 10 weeks. Feed Group II Nimodipine 20 mg/Kg once a day for 12 weeks and then observe the Group II for 10 weeks. Feed water to Group III and Group IV once a day for 12 weeks and then observe the Group III and Group IV for 10 weeks.

For Group I, put the rats on a frame, and fix them by using bandage. Put the heart rhythm generator on the tail of the rats, and radiate infrared ray with the hypertension therapy instrument to the belly of the rat. Keep the distance between the hypertension therapy instrument and the belly of the rat ranging from 15-20 cm.

Before the experiment, the blood pressure of the Group I, II, and III is 231.20±6.18(10)/171.70±6.93(10)mmhg, and the blood pressure of the Group IV is 158.00±7.72(6)/109.50±10.60(6)mmhg.

For Group I, 20±10 minutes after the first therapy, the blood pressure of the Group I drop to 208.70±14.40(10)/148.90±11.90(10) mmhg. For Group III, 1.5 hour±10 minutes after the first therapy, the blood pressure of the Group III only drops to 229.90±8.97(10)/168.00+8.12(10)mmhg.

At the 5th weeks of therapy, the blood pressure of the Group I drop to 232.67±16.36(9)/171.11±10.93(9)mmhg, and the blood pressure of the Group III only drops to 286.17±14.97(6)/213.25±15.84(4)mmhg.

During the 12 weeks therapy and 10 weeks observation, totally 154 days, the Group IV survive 154 days, Group III survive 44.10±21.79 days, only 28.64% of the Group IV, Group II survive 90.67+46.83 days, only 58.88% of the Group IV, and Group I survive 94.10±31.03, 61.10% of the Group IV.

During the 12 weeks therapy and 10 weeks observation, totally 154 days, all rats in the Group IV survive. At the $6^{th}$ week of the therapy, only 4/10rats of Group III survive, which 40% of the rats, and at the $12^{th}$ week of the therapy, all rats of Group III die. At the $6^{th}$ week of the therapy, 5/6rats of Group II survive, which is 83% of the rats, and at the $12^{th}$ week, 4/6 rats survive, which is 67.7% of the rats. At the $2^{nd}$ week of the observation, 3/6 rats of Group II survive, which is 50% of the rats, and at the 6$^{nd}$ week of the observation, 1/6 rats survive, which is 17% of the rats. At the 6$^{th}$ week of the therapy, 9/10 rats of Group I survive, which is 90% of the rats, and at the 12$^{th}$ week, 8/10 rats survive, which is 80% of the rats. At the 2$^{nd}$ week of the observation, 5/10 rats of Group I survive, which is 50% of the rats, and at the 6$^{nd}$ week of the observation, 2/10 rats survive, which is 20% of the rats.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A hypertension therapy instrument, comprising:
an infrared ray generator configured for radiating infrared ray onto a human body to treat hypertension;
a heart rate signal generator configured for sensing heart rate of the human body and outputs a heart rate signal containing heart rate information;
a controlling device comprising a controlling circuit configured for receiving the signal outputted by the heart rate signal generator and controlling a radiation intensity of the infrared ray generator based on the heart rate of the human body, in such a manner that the radiation intensity of the infrared ray generator changes with the heart rate of the human body to treat hypertension; and
a power supply supplying power to the infrared ray generator, the heart rate generator, and the controlling device; wherein the instrument further comprises a massager electrically connected with the infrared ray generator in parallel, so that strength of the massager changes with heart rate of a human body.

2. The hypertension therapy instrument, as recited in claim 1, wherein the controlling circuit further comprises an adjusting circuit comprising a silicon controlled rectifier and a circuit for controlling a conduction angle of the silicon controlled rectifier, so as to control the radiation intensity of the infrared ray generator.

3. The hypertension therapy instrument, as recited in claim 2, wherein the circuit for controlling a conduction angle of the silicon controlled rectifier is a resistor-capacitor phase shifting circuit.

4. The hypertension therapy instrument, as recited in claim 2, wherein the controlling circuit further comprises an amplifying and filtering circuit connected with the a heart rate signal generator for amplifying the heart rate signal received from the heart rate signal generator.

5. The hypertension therapy instrument, as recited in claim 4, wherein the heart rate signal generator is embodied as an electret condenser microphone.

6. The hypertension therapy instrument, as recited in claim 4, wherein the controlling circuit further comprises an isolation circuit connected between the amplifying and filtering circuit and the adjusting circuit.

7. The hypertension therapy instrument, as recited in claim 4, wherein the amplifying and filtering circuit further comprises a potentiometer $W_2$ to adjust the output level of the amplifying and filtering circuit so as to adjust the sensitivity of the hypertension therapy instrument.

8. The hypertension therapy instrument, as recited in claim 2, wherein the heart rate signal generator is embodied as an electret condenser microphone.

9. The hypertension therapy instrument, as recited in claim 2, wherein the circuit for controlling conduction angle of the silicon controlled rectifier comprises a potentiometer $W_1$ that can directly control the conduction angle of the silicon controlled rectifier so as to directly control output power of the infrared ray generator.

10. The hypertension therapy instrument, as recited in claim 6, wherein the isolation circuit comprises an LED and a photosensitive tube coupled with each other and connected with the amplifying and filtering circuit and the adjusting circuit respectively.

11. The hypertension therapy instrument, as recited in claim 10, wherein the isolation circuit further comprises a potentiometer $W_3$ and a switch $K_1$ connected in series are connected with the photosensitive tube in parallel for controlling the couple level between the LED and the photosensitive tube.

12. The hypertension therapy instrument, as recited in claim 6, wherein the infrared ray generator is embodied as an infrared ray lamp comprising a infrared ray bulb for radiating infrared ray.

13. The hypertension therapy instrument, as recited in claim 6, wherein the isolation circuit further comprises a potentiometer $W_3$ for controlling the couple level of the isolation circuit.

14. The hypertension therapy instrument, as recited in claim 1, wherein the heart rate signal generator is embodied as an electret condenser microphone.

15. The hypertension therapy instrument, as recited in claim 1, wherein the infrared ray generator is embodied as an infrared ray lamp comprising a infrared ray bulb for radiating infrared ray.

16. A hypertension therapy instrument, comprising:
an infrared ray generator configured for radiating infrared ray onto a human body to treat hypertension;
a heart rate signal generator configured for sensing heart rate of the human body and outputs a heart rate signal containing heart rate information;
a controlling device comprising a controlling circuit configured for receiving the signal outputted by the heart rate signal generator and controlling a radiation intensity of the infrared ray generator based on the heart rate of the human body, in such a manner that the radiation intensity of the infrared ray generator changes with the heart rate of the human body to treat hypertension; and
a power supply supplying power to the infrared ray generator, the heart rate generator, and the controlling device;
wherein the controlling circuit further comprises an adjusting circuit comprising a silicon controlled rectifier and a circuit for controlling a conduction angle of the silicon controlled rectifier, so as to control the radiation intensity of the infrared ray generator;
wherein the circuit for controlling a conduction angle of the silicon controlled rectifier is a resistor-capacitor phase shifting circuit;
wherein the controlling circuit further comprises an amplifying and filtering circuit connected with the heart rate signal generator for amplifying the heart rate signal received from the heart rate signal generator;
wherein the heart rate signal generator is embodied as an electret condenser microphone;

wherein the controlling circuit further comprises an isolation circuit connected between the amplifying and filtering circuit and the adjusting circuit;

wherein the isolation circuit comprises an LED and a photosensitive tube coupled with each other and connected with the amplifying and filtering circuit and the adjusting circuit respectively;

wherein the hypertension therapy instrument further comprises a massager electrically connected with the infrared ray generator in parallel, so that strength of the massager changes with heart rate of a human body;

wherein the infrared ray generator is embodied as an infrared ray lamp comprising a infrared ray bulb for radiating infrared ray;

wherein the circuit for controlling conduction angle of the silicon controlled rectifier comprises a potentiometer $W_i$ that can directly control the conduction angle of the silicon controlled rectifier so as to directly control output power of the infrared ray generator;

wherein the amplifying and filtering circuit further comprises a potentiometer $W_2$ to adjust the output level of the amplifying and filtering circuit so as to adjust the sensitivity of the hypertension therapy instrument;

wherein the isolation circuit further comprises a potentiometer $W_3$ and a switch $K_1$ connected in series are connected with the photosensitive tube in parallel for controlling the couple level of the isolation circuit between the LED and the photosensitive tube.

* * * * *